(12) United States Patent
Fine et al.

(10) Patent No.: US 6,804,002 B2
(45) Date of Patent: Oct. 12, 2004

(54) METHOD AND DEVICE FOR MEASURING CONCENTRATION OF GLUCOSE OR OTHER SUBSTANCES IN BLOOD

(75) Inventors: Ilya Fine, Rehovot (IL); Boris Fikhte, Rehovot (IL); Mark Vinokur, Rehovot (IL)

(73) Assignee: Orsense Ltd., Rehovot (IL)

( * ) Notice: Subject to any disclaimer, the term of this patent is extended or adjusted under 35 U.S.C. 154(b) by 0 days.

(21) Appl. No.: 10/297,839
(22) PCT Filed: Jun. 11, 2001
(86) PCT No.: PCT/IL01/00529
§ 371 (c)(1), (2), (4) Date: Dec. 11, 2002
(87) PCT Pub. No.: WO01/96872
PCT Pub. Date: Dec. 20, 2001

(65) Prior Publication Data
US 2003/0137650 A1 Jul. 24, 2003

(30) Foreign Application Priority Data
Jun. 11, 2000 (IL) ................................. 136673

(51) Int. Cl.[7] .............................. G01J 4/00; A61B 5/00
(52) U.S. Cl. ....................................... 356/364; 600/322
(58) Field of Search ..................... 356/39–40, 364–370; 600/322–326; 369/364, 366, 368; 128/664–666

(56) References Cited

U.S. PATENT DOCUMENTS 4,714,341 A * 12/1987 Hamaguri et al. ............ 356/41
4,901,728 A 2/1990 Hutchison (List continued on next page.)

FOREIGN PATENT DOCUMENTS

| EP | 0 030 610 | 6/1981 |
| EP | 0 424 934 A2 | 5/1991 |
| FR | 2 576 106 | 7/1986 |
| WO | WO94/13199 A1 | 6/1994 |
| WO | WO96/39926 A1 | 12/1996 |
| WO | WO99/65384 A1 | 12/1999 |

OTHER PUBLICATIONS

Goodall et al., "Polarlmetric Stopped–Flow Apparatus", Rev. Sci. Instrum., vol. 46, No. 4, pp. 391–397 (Apr. 1975).

(List continued on next page.)

Primary Examiner—Michael P. Statira
(74) Attorney, Agent, or Firm—Browdy and Neimark, P.L.L.C.

(57) ABSTRACT

A method and device for optical measurements are presented for determining the concentration of a substance in patient's blood. Optical measurement sessions are applied to a measurement location in a blood containing medium during certain time period. The optical measurements include illumination of the measurement location with incident light of at least one selected wavelength, detection, at each measurement session, of at least two light responses of the medium characterized by at least two different polarization states of detected light, respectively, and generation of data representative thereof. Measured data so obtained is in the form of at least two time variations of the light responses of the medium characterized by different polarization states of detected light, respectively, a relation between the time variations being indicative of the concentration of the substance in blood.

53 Claims, 10 Drawing Sheets

U.S. PATENT DOCUMENTS

| | | | |
|---|---|---|---|
| 5,209,231 A | | 5/1993 | Cote et al. |
| 5,398,681 A | | 3/1995 | Kupershmidt |
| 5,448,992 A | * | 9/1995 | Kupershmidt ............... 600/347 |
| 5,533,509 A | | 7/1996 | Koashi et al. |
| 5,551,422 A | | 9/1996 | Simonsen et al. |
| 5,676,143 A | | 10/1997 | Simonsen et al. |
| 5,687,721 A | | 11/1997 | Kuhls |
| 5,692,504 A | | 12/1997 | Essenpreis et al. |
| 5,956,144 A | * | 9/1999 | Kaplan et al. .............. 356/364 |
| 5,983,120 A | * | 11/1999 | Groner et al. .............. 600/310 |
| 6,015,969 A | * | 1/2000 | Nathel et al. .......... 250/227.27 |

OTHER PUBLICATIONS

McNichols et al., "Optical Glucose Sensing in Biological Fluids: An Overview", *Journal of Biomedical Optics*, vol. 5(1), pp. 5–16 ( Jan. 2000).

Reiss, "Glucose– and Blood–Monitoring Systems Vie for Top Spot", *Biophotonics International*, pp. 43–45 (May/Jun. 1997).

Robinson, "Blood Analysis: Noninvasive Methods Hover on Horizon", *Biophotonics International*, pp. 48–52 (May/ Jun. 1998).

* cited by examiner

METHOD AND DEVICE FOR MEASURING CONCENTRATION OF GLUCOSE OR OTHER SUBSTANCES IN BLOOD

FIELD OF THE INVENTION

This invention is in the field of optical measurement techniques, and relates to a method and deuce for measuring the concentration of glucose or other substances in blood, such as cholesterol albumin, etc. The present invention is useful for both in vitro and in vivo measurements.

BACKGROUND OF THE INVENTION

Optical methods for determining the chemical composition of blood are known and are typically based on spectrophotometric measurements enabling the indication of the presence of various blood constituents based on known spectral behaviors of these constituents. These spectrophotometric measurements can be effected either In vitro or in vivo. The measurements in vitro are invasive, i.e., require a blood sample to be physically withdrawn and examined. At present, these measurement have become unpopular, due to the creasing danger of infection.

The only accepted non-invasive optical measurement technique for measuring blood parameters is pulse oximetry. However, pulse oximetry provides solely for the determination of oxygen saturation in blood. For other blood parameters, the determination is too problematic, because their absorption spectral behavior in red-NIR regions is not as reliable as for oxygenized and non-oxygenized hemoglobin. As a result, patients suffering from diabetes who need to control their disease by monitoring their blood glucose levels, especially after walking, eating or exercising, still have to draw a small blood sample from their fingertip, apply and use monitoring strips and use a small machine.

Various techniques have been developed aimed at facilitating the measurement of the concentration of glucose in a patient's blood. These techniques are disclosed, for example, in the following publications:

"Blood Analysis: Noninvasive Methods Hover on Horizon", K. Robinson, Biophotonics International, May/June 1998;

"Glucose- and Blood-Monitoring Systems Vie for Top Spot", Susan M. Reiss, Biophotonics International, May/June 1997;

"Optical Glucose Sensing in Biological fluids: and Overiew", Roger J. McNichols, Gerard Cote, Journal of Biomedical Optics, January 2000, Vol. 5. No. 1, pp. 5–16; and U.S. Pat. Nos. 5,209,231; 5,398,681; 5,448,992; 5,687,721; 5,692,504; 5,551,422; 5,676,143; 5,533,509; 5,687,721; 4,901,728.

Most of the above techniques are based on the known phenomenon consisting in that glucose, being an optically active medium, rotates polarized light, and the higher the concentration of glucose, the greater the rotation.

According to all prior art techniques, measurements are applied to a blood flow containing medium during the state of normal blood flow, and the measured signals are pulsatile-related signals.

A different technique for measuring various blood-related parameters has been developed and disclosed in WO 99/65384, assigned to the assignee of the present application. This technique utilizes the so-called occlusion-release mode, wherein over-systolic pressure is applied to a patient's blood perfused fleshy medium so as to create the state of blood flow cessation at a measurement location. Optical measurements are applied during a time period including cessation time, during which the state of blood flow cessation is maintained, and time dependencies of "non-pulsatile" light responses of the medium are determined for at least two wavelengths of incident radiation. This technique enables to significantly enhance the light response signal, as compared to that obtained with the pulse oximetry.

GENERAL DESCRIPTION OF THE INVENTION

The main idea of the present invention is based on measuring the time variations of light responses of a blood containing medium corresponding to different polarization states of detected light. Generally speaking, the present invention is based on establishing the correlation between the kinetics of changes in the properties of blood containing scattering affecting or optically active substances (mainly, glucose), and the kinetics of changes in the state of polarization of linearly polarized radiation scattered by tissue containing blood vessels and capillaries.

Thus, according to one aspect of the present invention, there is provided a method of optical measurements for determining the concentration of a substance in a patient's blood, the method comprising the steps of performing optical measurement sessions within a certain period of time by illuminating a measurement location in a blood containing medium with incident light of at least one selected wavelength, detecting, at each measurement session, at least two light responses of the medium characterized by at least two different polarization states of detected light, respectively, and generating data representative thereof and obtaining measured data in the form of at least two time variations of the light responses of the medium, a relation between the time variations being indicative of the concentration of the substance in blood It should be understood that the term "measurement session" signifies at least two measurements, taken either sequentially or simultaneously, including the illumination of the measurement location with at least one wavelength of incident light and the detection of at least two light responses characterized by different polarization states of the detected light, respectively. By performing more than one measurement session, either continuously or timely separated, the time variations of light responses of different polarization states are obtained.

Preferably, the present invention utilizes the principles of the above-indicated occlusion-release technique to apply optical measurements during the state of blood flow cessation at a measurement location. Accord to the present invention, however, measurements are carried out in a manner to detect at least two light responses of the medium characterized by two different states of polarization, respectively, and to measure time variations of the light responses. To this end, pressure is applied to a location on the blood containing medium (e.g, over-systolic pressure applied to the patient's blood perfused fleshy medium, in the case of non-invasive measurements), and the measurement location to which the optical measurement sessions are applied, is located downstream of the pressed location with respect to the blood flow direction. The application of pressure causes artificial change in the velocity of blood, namely, causes the state of blood flow cessation at a location downstream of the pressurized location. The artificial change in the blood results in the aggregation of red blood cells (Rouleaux effect) with time-varying shape and size of aggregates. At the state of the blood flow cessation, when there is actually no blood flow, no shear forces prevent the erythrocytes' aggregation process. Hence, the light response (transmission or reflection) of the blood perfused fleshy medium at the state of the blood flow cessation can be considered as the time dependence of scattering in a system growing scatterers.

Glucose, being the main optically active substance in blood, influences the optical characteristics of scattered and partly absorbed radiation in a complicated manner. More specifically, glucose introduces changes in the ratio of refraction indices of erythrocytes and surrounding plasma, and introduces spectrally dependent optical rotation (rotary dispersion). These-factors lead to dynamic changes in the state of polarization, in particular the polarization or depolarization degree, under the condition of kinetic changes in the aggregates in the case of periodical application of occlusion (occlusion-release sessions).

Dynamic multiple scattering increases the optical path of radiation scattered from a blood sample and, consequently, the angle of rotation of polarization of incident light. Additionally, it is known that the state of polarization of incident light affects the light scattering properties (via the Stokes parameters). Thus, the results of the transmission or reflection measurement will be governed by the state of polarization of the incident light. This means that any change in the relative refraction index of the scatterer (i.e., red blood cell in the case of blood) will affect the measured light intensity differently depending on the state of polarization of the incident light. Since the concentration of the scattering affecting substance in blood (e.g., an optically active substance such as glucose) affects the relative refractive index, any parameter utilizing the combination of two or more different polarization measurements will be sensitive to the concentration of this substance.

Thus, the optically active or scattering affecting substance in a medium (e.g., glucose in blood) may influence the optical characteristics of the medium in two different ways: (1) through the optical activity and (2) through the polarization dependent scattering. The optical response of the system in the polarization dependent measurement set-up provides additional information relating to the substance concentration in the medium.

In order to pick up substantially multiple-scattered radiation, an analyzer means of a radiation receiving unit is mounted such that its plane of preferred potion is oriented at a predefined angle (for example, orthogonal) to that of a polarizer means of a radiation source.

Generally, the measurements may be carried out with one wavelength of incident radiation lying in visual or near infrared spectra, but with two or more different polarization states of either the incident or the collected radiation. However, to increase the accuracy of measurement, taking into account the dispersion of optical rotation, the measurements with different polarization states of the light response may be repeated for two or more different wavelengths of incident radiation. To decrease incidental fluctuations, multiple measurement sessions are performed by the alternation of aggregation-deaggregation cycles (i.e., multiple occlusion-release sessions) with the synchronization of start and end points of measurements and with subsequent statistical averaging By standardizing the measurement conditions and performing preliminary calibration on blood samples with known concentrations of glucose, the method of the present invention enables to determine the level of glucose in blood in-vitro, as well as in-vivo.

Thus, the method consists of determining quantitative relationship between the kinetics of changes in polarized light (while at the "flow-stop" mode) passed through an absorbing and scattering medium that contains a certain concentration of scattering affecting substance, and the concentration of this substance. The medium under measurements is the patient's blood perfused fleshy medium, e.g., his finger, when dealing with in vivo measurements, or a suspension of RBC in cuvette, in the case of in vitro measurements.

The method consists of two stages: At the first stage, correlation between the concentration of a substance (glucose) and a predefined, non-dimensional parameter, R, is measured. This measurable parameter R is indicative of some kind of a mathematical relation between the two opto-kinetic signals (occlusion curves), generated by scattering, absorption and polarization changes, occurring during the state of blood aggregation.

For example, the parameter R may present a parametric slope (tangent of the angle of inclination) of a curve representative of multiple scattered polarized light. Graphically, this is an inclined line in coordinates $(T_1-T_2)$, or $(\log T_1-\log T_2)$, wherein $T_1$ is the light response of the medium with one state of polarization (e.g., linearly polarized light), and $T_1$ is the light response of the medium with another state of polarization. These different light responses may, for example, be obtained by illuminating the medium with incident light of the same wavelength but different polarization states. Since this curve is indicative of the kinetic curves reflecting the complete attenuation of the polarized and unpolarized light, respectively, it actually presents a curve of the multiple scattered polarized light.

Another possible example of such a parameter R may be the degree of depolarization of the collected light, which is the function of time and can be calculated as follows: $(t_1-T_2)/(T_1+T_2)$. This function is different for different wavelengths of incident light.

The measurable parameter R (e.g., parametric slope of the curve $T_1(T_2)$ or degree of depolarization) is indicative of the glucose concentration in the blood under measurements. To determine the glucose concentration $C_{gl}$, reference data in the form of a calibration curve $R(C_{gl})$ is previously obtained. The calibration curve may be different for different measurement devices. Thus, at the second stage, the concentration of glucose is determined using the calibration curve.

The calibration curve may be obtained by applying the measurements of the present invention to blood samples (or plurality of patients) with the known concentration of glucose. The calibration curve may be plotted with respect to the same patient, by causing changes in the concentration of glucose in his blood and applying the technique of the present invention for determining the corresponding value of the parameter R.

Thus, according to another aspect of the present invention, there is provided a method of optical measurements for determining the concentration of a substance in a patient's blood, the method comprising the steps of:

creating a state of blood flow cessation within a measurement location in a blood flow containing medium, and maintaining said state during a certain cessation time;

performing optical measurement sessions within a time period including said certain cessation time, the optical measurements including illumination of the measurement location with incident light of at least one selected wavelength, detection, at each measurement session, of at least two light responses of the medium characterized by at least two different polarization states of detected light, respectively, and generation of data representative thereof;

obtaining measured data in the form of at least two time variations of the light responses of the medium, a relation between the time variations being indicative of the concentration of the substance in blood.

According to yet another aspect of the present invention, there is provided a method of optical measurements for non-invasively determining the concentration of a substance in a patient's blood, the method comprising the steps of:

applying over-systolic pressure to a location on the patient's blood perfused fleshy medium, thereby creating a state of blood flow cessation within a measurement location downstream of the location of application of pressure, and maintaining said state during a certain cessation time;

performing optical measurement sessions within a time period including said certain cessation time, the optical measurements including illumination of the measurement location with incident light of at least one selected wavelength, detection at each measurement session, of at least two light response of the medium characterized by at least two different polarization states of detected light, respectively and generation of data representative thereof;

obtaining measured data in the form of at least two time variations of the light responses of the medium, a relation between the time variations being indicative of the concentration of the substrate in blood.

According to yet another aspect of the present invention, there is provided a method for determining the concentration of a substance in a patient's blood, the method comprising the steps of:

providing reference data indicative of a preset measurable parameter as a function of values of said concentration;

creating a state of blood flow cessation within a measurement location in a cessation time;

performing optical measurement sessions within a time period including said certain cessation time, the optical measurements including illumination of the measurement location with incident radiation of at least one selected wavelength, detection, at each measurement session, of at least two light responses of the medium characterized by at least two different polarization states of detected light, respectively, and generation of measured data representative thereof;

utilizing the measured data for obtaining measurement results in the form of at least two kinetic curves of the light responses of the medium as functions of time corresponding to the different polarization states of the detected light;

analyzing said at least two kinetic curves for calculating said certain parameter indicative of relation between them, and utilizing the calculated value and said reference data for determining the concentration of the substance in the patient's blood.

According to yet another aspect of the present invention, there is provided a method for non-invasively determining the concentration of a substance in a patient's blood, the method comprising the steps of:

providing reference data indicative of a preset measurable parameter as a function of values of said concentration;

applying over-systolic pressure to a location of the patient's blood perfused fleshy medium, thereby creating a state of blood flow cessation within a measurement location downstream of the location of application of pressure with respect to the blood flow direction, and maintaining said state of the blood flow cessation during a certain cessation time being insufficient for irreversible changes in the fleshy medium;

performing optical measurement sessions within a period including said certain cessation time, the optical measurements including illumination of the measurement location with incident light of at least one selected wavelength detection, at each measurement session, of at least two light responses of the medium characterized by at least two different polarization states of detected light, respectively, and generation of data representative thereof;

utilizing the measured data for obtaining measurement results in the form of at least two kinetic curves of the light responses of the medium as functions of time corresponding to the different polarization states of the detected light;

analyzing said at least two kinetic curves for calculating said certain parameter indicative of relation between them, and utilizing the calculated value and said reference data for determining the concentration of the substance in the patient's blood.

To detect light beams with different polarization states, one of the following implementations is possible:

(1) The medium (at the measurement location) is illuminated with two beams of incident radiation having different polarization states (e.g., polarized and unpolarized light), and a specific polarization filtering, common for both beams of the incident light, is applied at the detection side.

To this end, the illumination unit may comprise two light sources (e.g., sequentially operable) generating two light beams, respectively, and comprises either a single polarizer mounted stationary in the optical path of one of the generated beams, or two polarizers with different orientations of their planes of preferred polarization mounted in the optical paths of the two beams, respectively. Alternatively, a single light source can be utilized to generate two timely separated beams of incident light. In this case, a polarizer of the illumination unit is shiftable between its operative and inoperative positions, being in and out of the optical path of the incident beam, respectively.

As for the detection means, it comprises a detector unit equipped with an analyzer mounted stationary in the optical path of light returned from the medium (e.g., transmitted), provided the plane of preferred polarization of the analyzer is specifically oriented with respect to that of the polarizer(s) of the illumination unit.

(2) The medium is illuminated with an incident beam having a predefined polarization state, and different polarization filtering is applied at the detection side with respect to two spatially separated light components of a transmitted (or reflected) beam, respectively. For this purpose, the illumination unit comprises a single light source emitting a beam of light, and a single polarizer mounted in the optical path of the emitted beam. The detection means comprises a pair of detector units and either two differently oriented analyzers mounted in front of the detector units, respectively, or a single analyzer mounted in front of one of the detector units only.

According to yet another broad aspect of the present invention, there is provided a measurement system for determining the concentration of a substance in a patient's blood, the system comprising:
  a measurement device that comprises a pressurizing assembly for applying pressure to a blood flow containing medium, so as to create a state of blood flow cessation at a measurement location in the medium downstream of the pressurized location with respect to the direction of blood flow, and a measuring unit for performing optical measurement sessions at said measurement location, the measuring unit comprising an illumination system and a light collection/detection system which are operable to detect, at each measurement session, at least two light responses of the medium characterized by at least two different polarization states of detected light, respectively, and generate measured data representative thereof; and
  a control unit connectable to the measurement device for selectively operating said measuring unit and said pressuring assembly, such that the state of blood flow cessation is maintained during a certain cessation time and the optical measurement sessions are performed within a time period including said cessation time,
    the control unit being responsive to said measured data to determine time variations of said at least two light responses of the medium corresponding to at least two different polarization states of the detected light, and analyze the time variations for determining a preset parameter measured as a relation between the time variations, and determining the concentration of said substance using reference data indicative of the preset measurable parameter as a function of values of the substance concentration.

According to yet another aspect of the present invention, there is provided a measurement system for non-invasively determining the concentration of a substance in a patient's blood, the system comprising:
  a measurement device that comprises a pressurizing assembly operable to apply over-systolic pressure to a location on the patient's blood perfused fleshy medium, so as to create a state of blood flow cessation at a measurement location in the medium located downstream of the location of the application of pressure; and comprises a measuring unit operable to perform optical measurement sessions to said measurement location, the measuring unit comprising an illumination system and a light collection/detection system which are operable so as to detect at least two light responses of the medium characterized by at least two different polarization states of detected light respectively, and generate measured data representative thereof; and
  a control unit connectable to the measurement device for selective operating said measuring unit and said pressurizing assembly, such that the state of blood flow cessation is maintained during a certain cessation time being insufficient for irreversible changes in the fleshy medium, and the optical measurement sessions are performed within a time period including said cessation time, the control unit being responsive to said measured data to determine time variations of said at least two light responses of the medium corresponding to at least two different polarization states of the detected light, and analyze the time variations for determining a preset parameter measured as a relation between the time variations, and determining the concentration of said substance using reference data indicative of the preset measurable parameter as a function of values of the substance concentration.

According to yet another aspect of the present invention, there is provided a measurement device for performing non-invasive optical measurement for determining the concentration of a substance in a patient's blood, the device comprising
  a pressurizing assembly operable to apply over-systolic pressure to a location on the patient's blood perfused fleshy medium, so as to create a state of blood flow cessation at a measurement location in the medium located downstream of the location of application of pressure, and to maintain said state during a certain cessation time being insufficient for irreversible changes in the fleshy medium; and
  a measuring unit operable to perform optical measurement sessions at said measurement location within a time period including said cessation time, the measuring unit comprising an illumination system and a light collection/detection system which are operable to detect, at each measurement session, at least two light responses of the medium characterized by at least two different polarization states of detected light, respectively, and generate measured data representative thereof, the measured data being indicative of time variations of said at least two light responses of the medium corresponding to at least two different polarization states of the detected light, a relation between said time variations being indicative of the concentration of said substance.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

Figure 1A:
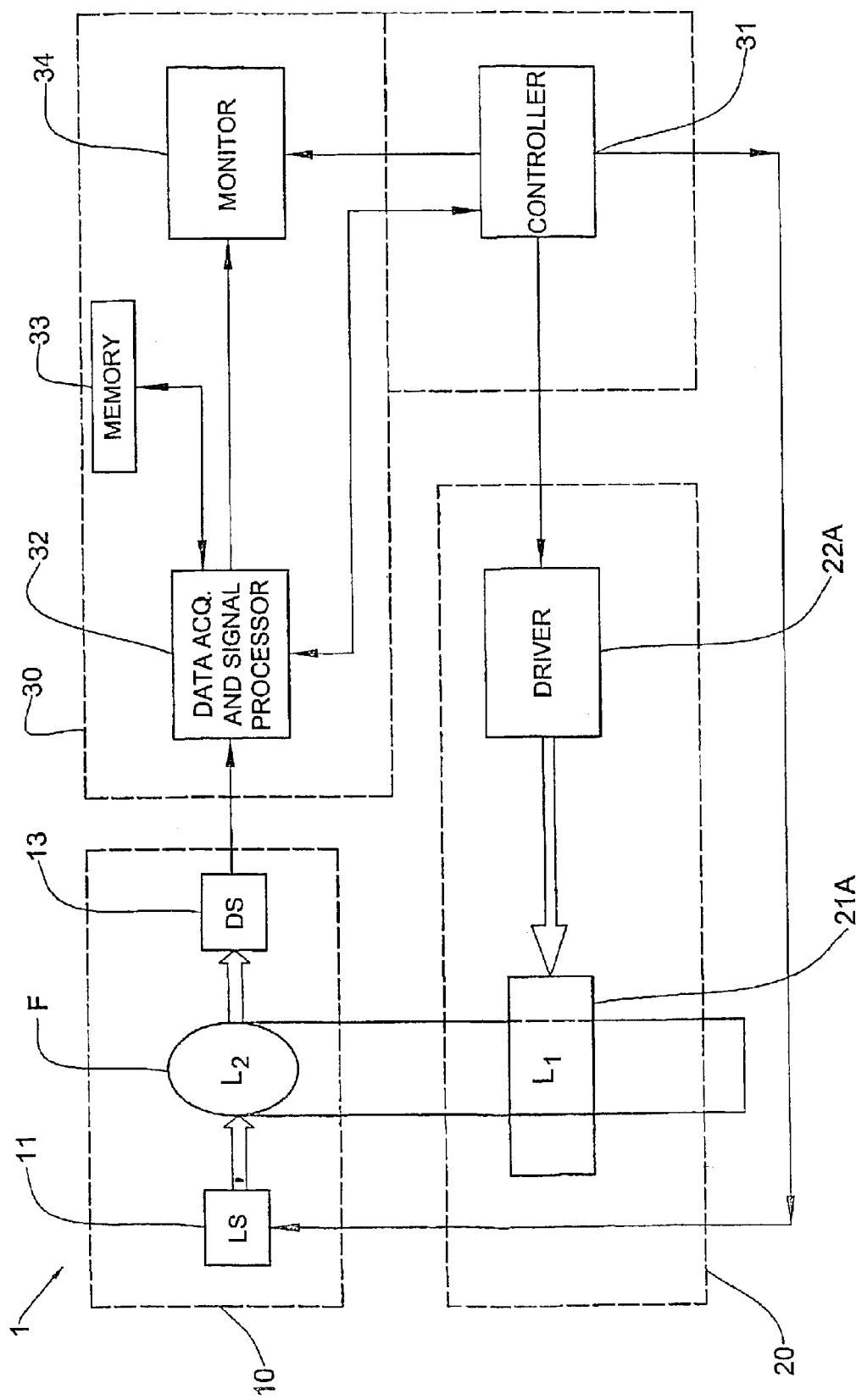
FIG. 1A is a schematic illustration of a measurement device according to the invention used for non-invasive measurements of glucose concentration.

Referring to FIG. 1A, there is illustrated a measurement system 1, according to one embodiment of the invention. The system is intended for in vivo optical measurements of patient's blood parameters utilizing an occlusion-release-based technique. The system 1 comprises a measurement device, which is applied to the patient's finger F (constituting a blood containing medium or BCM) and a control unit.

The measurement device comprises such main constructional part as a measuring unit (or optical sensor), generally designated 10, and a press assembly (the so-called "occluder") 20. Control unit 30 is connectable to the measurement device, namely, to the measuring unit 10 and to the occluder 20 to selectively operate each of then. The occluder 20 is operable by the control unit 30 to apply over-systolic pressure to a first location $L_1$ on the finger F and maintain the pressure during a certain time period (cessation time). Such application of the over-systolic pressure at the location $L_1$ results in the creation of the state of blood flow cessation at a second location $L_2$, which is located downstream of the first location $L_1$ with respect to the blood flow direction, and maintenance of the blood flow cessation state during the cessation time, which is insufficient for irreversible changes in the fleshy medium. The measuring unit 10 is operable by the control unit 30 to apply optical measurements at the measurement location $L_2$ during the cessation time.

In the present example, the occluder 20 is composed of a cuff 21A wrapping the finger at the location $L_1$ (finger's basis), and a driver 22A coupled to the cuff 21A for operating the squeezing thereof. The measuring unit 10 includes an illumination system 11 and a light collection/detection system 13, which, in the present example, is accommodated so as to detect light transmitted through the medium at the measurement location $L_2$ (finger tip). It should, however, be understood that by appropriately designing the measurement unit, light reflected from the medium could be detected.

The control unit 30 comprises a controller 31 which is coupled to the driver 22A, to the illumination system 11, and to the output of the detection system 13 via a data acquisition and signal processing (DASP) utility 32. Also provided in the control unit is a memory 33 for storing certain reference data (as will be described more specifically further below), and a monitor 34 interconnected between the controller 31 and DASP utility 32.

Figure 1B:
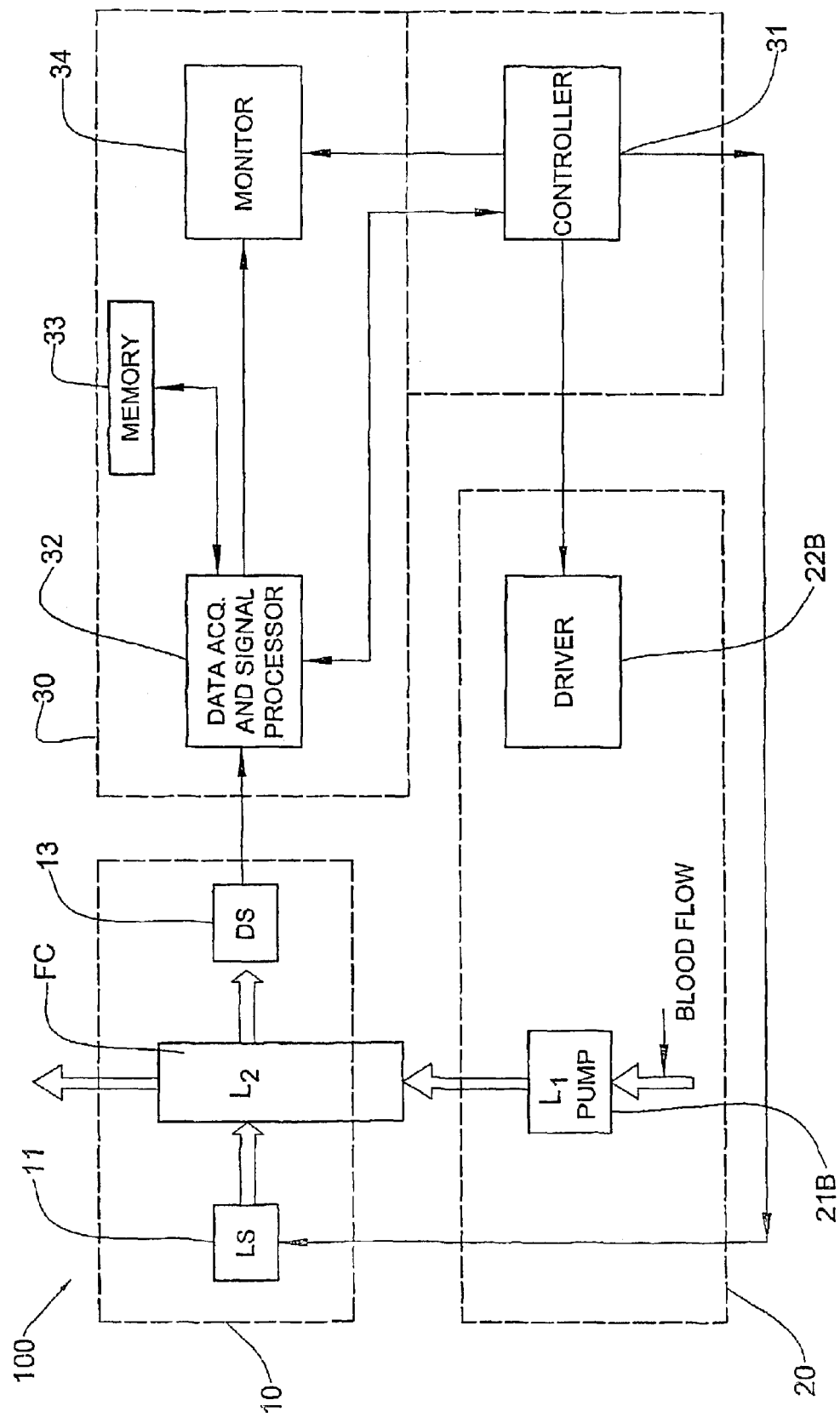
FIG. 1B is a schematic illustration of a measurement device according to the invention used for invasive measurements of glucose concentration.

FIG. 1B illustrates a measurement system 100 according to another example of the invention aimed at in vitro measurements. To facilitate understanding the same reference numbers are used for identifying those components, which are common in the systems 1 and 100. A flow of the patient's blood sample is directed through a flow cuvette FC, which thus presents a blood containing medium (BCM) with the measurement location $L_2$ thereinside. The occluder 20 is a pneumatic assembly composed of a peristaltic pump 21B associated with its driver 22B connected to the control unit 30 and operated for creating the state of blood flow cessation in the flow cuvette FC.

For the purposes of tile present invention, the construction and operation of the measuring unit (i.e., illumination and detection systems) is aimed at providing the detection of at least two time variations of light responses (transmission) of the BCM corresponding to at least two different polarization states of detected light, respectively. To this end, the measuring unit is operable to perform at least two timely separated measurement sessions, each including the illumination of the measurement location with at least one wavelength of incident light, and the detection of light responses of the medium characterized by different polarization states of the detected light, respectively. FIGS. 2A–2E illustrate different possible examples of the implementation of the illumination and detection systems.

Figure 2A:
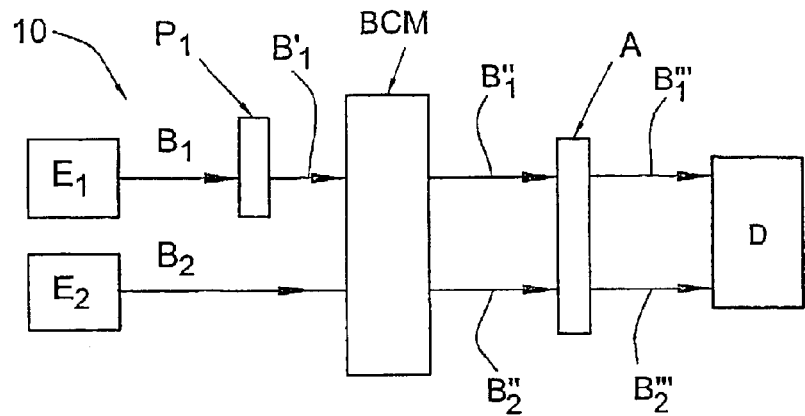
FIGS. 2A to 2E illustrate five different examples, respectively, of a measurement unit according to the invention suitable to be used in the device of either FIG. 1A or FIG. 1B.
Figure 2B:
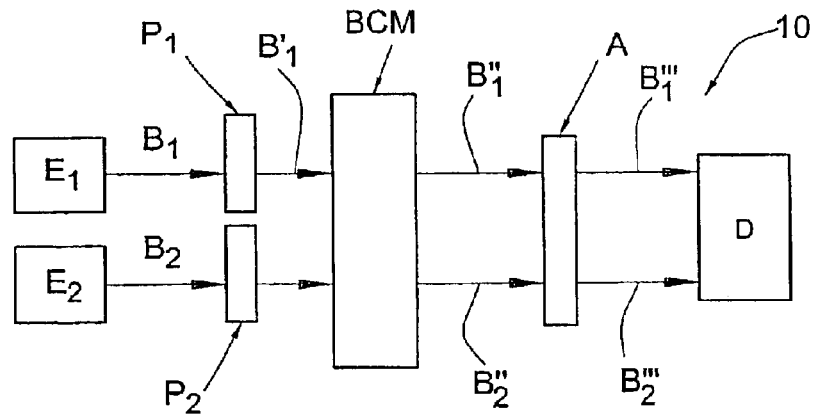
Figure 2C:
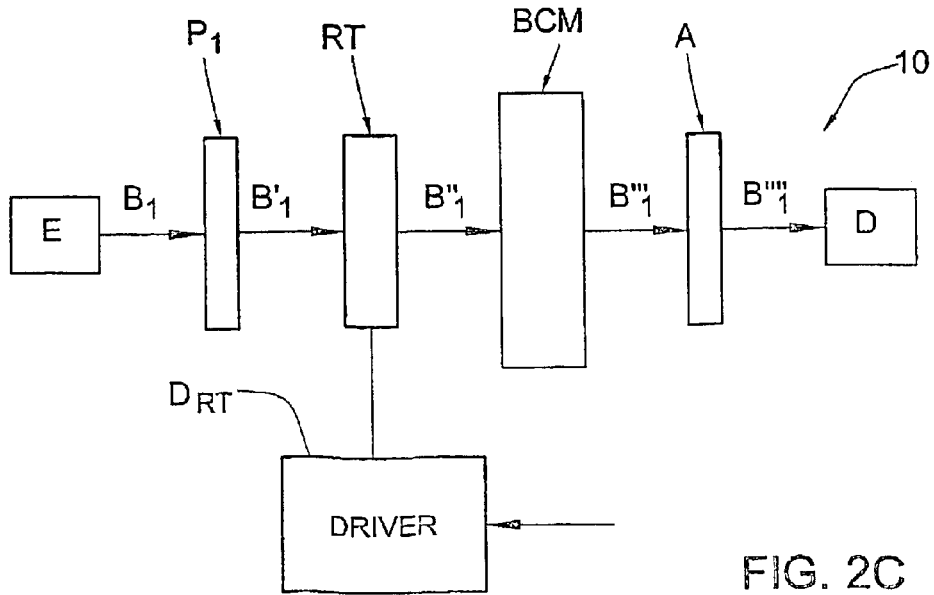
Figure 2D:
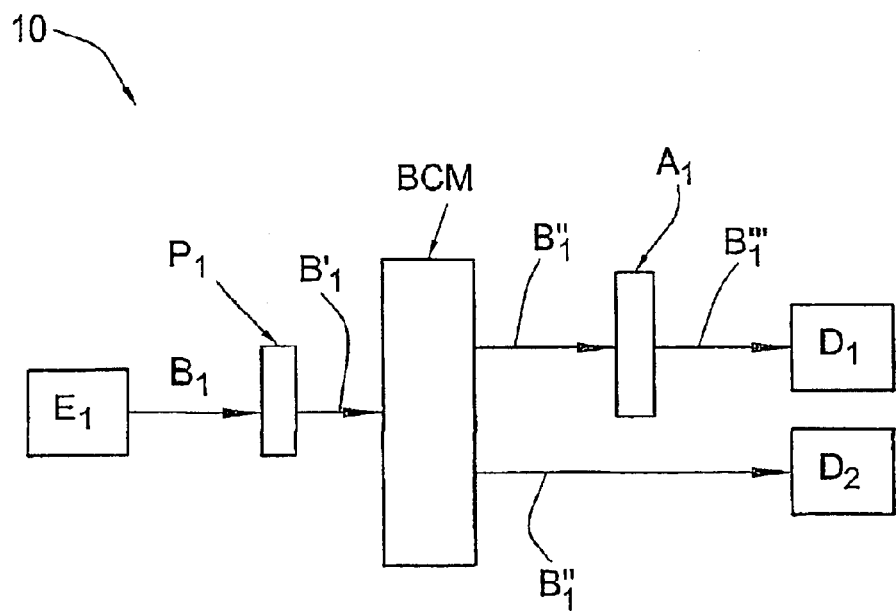
Figure 2E:
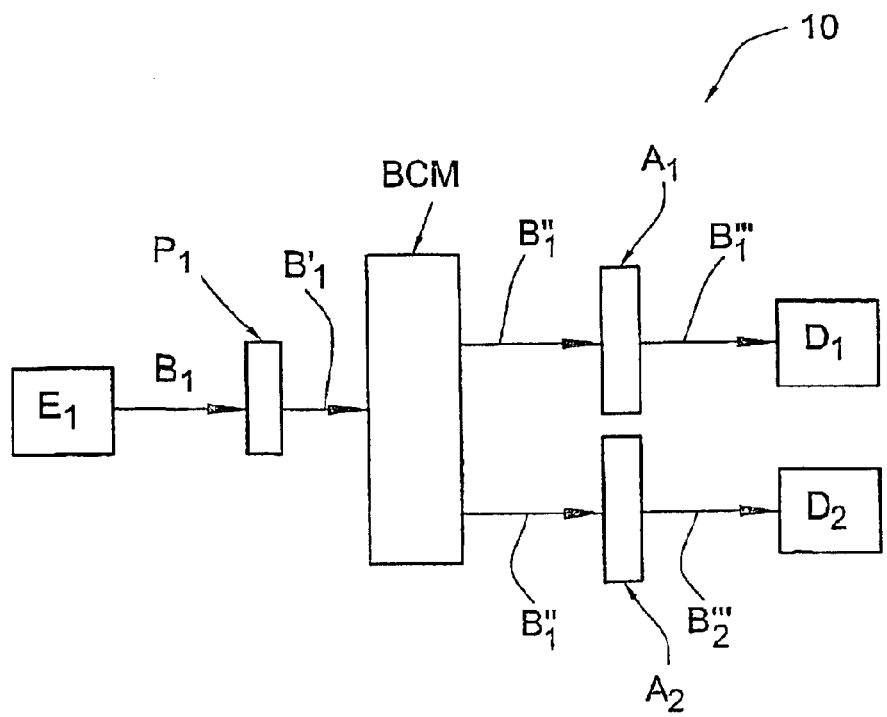

According to the examples of FIGS. 2A–2C, the difference in the polarization states of the detected light beams is introduced at the illumination stage, and consequently, two incident light beams are timely separated. In the examples of FIGS. 2D and 2E, this difference is introduced by performing polarization filtering at the light collection/detection stage, and therefore, a single incident light beam can be generated for performing two measurement sessions.

In the example of FIG. 2A, the illumination on system 11 comprises an illuminator including two light sources or emitters $E_1$ and $E_2$ (e.g., LEDs) generating light beams $B_1$ and $B_2$, respectively, and comprises a poor $P_1$ installed in the optical path of one of the emitted beams—beam $B_1$ in the present example. Thus, beams $B_1'$ and $B_2$ impinging onto the BCM are, respectively, polarized and unpolarized beams. Beams $B_1$ and $B_2$ have the same selected wavelength in the visual or near infrared spectra. The light sources $E_1$ and $E_2$ may be sequentially operated by the control unit, so as to provide time separation between the incident beams $B_1''$ and $B_2$.

The detection system 13 comprises a detector Unit D (e.g., photodetector) and an analyzer A mounted in the optical path of light ensuing from the BCM, namely beams $B_1''$ and $B_2''$ corresponding, respectively, to the incident beams $B_1'$ and $B_2$. The analyzer A has a plane of preferred polarization oriented different from that of the polarizer $P_1$, being for example, orthogonal thereto. The detector unit D detects a first light response $B_1'''$ and a second light response $B_2'''$ of the BCM characterized by different polarization states of detected light.

To perform at least two timely separated measurement sessions (to obtain time variations of the light responses), the illumination with the pair of beams $B_1'$ and $B_2$ is repeated at different moments of time, or is performed continuously, in which case, the detection is carried out at different moments of time. It should be understood that although a common diagram is used for illustrating the light propagation within the measuring unit 10 with respect to both incident beams, the corresponding diagram parts relate to timely separated events (measurement sessions).

It should be noted, although not specifically shown, that the same effect of providing two incident beams with different polarization states may be achieved by utilizing a single light source and a polarizer, which is shiftable between its operative and inoperative position, being, respectively, in and out of the optical path of the incident beam. Alternatively, a polarizing assembly may be installed stationary in the optical path of the incident beam and selectively operable to change the plane of preferred polarization.

According to the example of FIG. 2B, two different polarizers $P_1$ and $P_2$ (ie., with different orientations of their planes of preferred polarization) are installed in the optical paths of emitted beams $B_1$ and $B_2$ respectively, thereby providing beams $B_1'$ and $B_2'$ propagating towards the BCM.

As for the detection system, its analyzer A has a predefined orientation of its plane of preferred polarization, different from that of the polarizer $P_1$ and of the polarizer $P_2$. Each of beams $B_1''$ and $B_2''$ ensuing from the BCM passes through the analyzer $A_3$, and is received by the detector D presenting the respective light response of BCM, ie., $B_1'''$ and $B_2'''$.

In the example of FIG. 2C, a single light emitter $E_1$ is used, and a single polarizer $P_1$ is installed in the optical path of emitted beam $B_1$. Accommodated between the polarizer $P_1$ and the BCM under measurements is a retarder RT, associated with a driver $D_{RT}$ so as to operate in different operational modes with respect to the different emitted beams, respectively. The retarder is either switchable between two operational modes or tunable to provide continuously varying operational modes. The construction and operation of a retarder are known per se, and therefore need not be specifically described, except to note that the retarder may utilize a ferroelectric liquid crystal material (switchable), or a voltage dependent (tunable) liquid crystal (nematic) material.

The polarized light beam $B_1'$ propagating towards the BCM passes through the retarder RT, which affects the orientation of the plane of polarization of the linearly polarized light. Light beam $B_1''$ ensuing from the retarder RT propagates through the BCM producing an output light beam $B_1'''$, propagating towards the detection system 13. The latter comprises a singe analyzer A having the plane of preferred polarization specifically oriented with respect to that of the polarizer $P_1$. Thus, light $B_1''''$ ensuing from the analyzer A presents the light response of the medium to be detected by the detector unit. It should be understood, that in order to obtain the time dependencies of different light responses (i.e., corresponding to different polarization states of detected light), the illumination/detection session is repeated at least twice (i e., at different moments of time), each session including two measurements with different polarization states of incident light, respectively.

According to the examples of FIGS. 2D and 2E, the illumination system 11 comprises a single light emitter $E_1$ and a single polarizer $P_1$ in the optical path of emitted beam $B_1$. The detection system 13 comprises two detector units $D_1$ and $D_2$, and is capable of simultaneously (ie., during the same measurement session) detecting light responses of different polarization states of light, respectively.

To this end, as shown in the example of FIG. 2D, one of the detector units ($D_1$) is provided with the analyzer $A_1$, while the other detector unit ($D_2$) is not. Thus, a polarized beam $B_1'$ impinges onto the BCM. A transmitted beam $B_1''$ partly passes through the analyzer $A_1$ resulting in the light response $B_1'''$ received by the detector $D_1$, while the other presents a light response $B_1''$ of the medium directly received by the detector $D_2$. These light responses $B_1'''$ and $B_1''$ are characterized by different polarization states.

In the example of FIG. 2E, both detector units $D_1$ and $D_2$ are equipped with analyzers $A_1$ and $A_2$, respectively. Light responses $B_1'''$ and $B_2'''$ detected by the units $D_1$ and $D_2$, respectively, have different polarization states.

The system 1 (or 100) operates in the following manner. The control unit 30 operates the occluder 20 for creating a state of blood flow cessation at the measurement location $L_2$, maintaining this state over a certain time period (cessation time), and then releasing the pressure. In other words, the device operates in the so-called "occlusion-release mode". Upon the creation of the state of blood flow cessation, the control unit 30 actuates the measuring unit 10 to carry out at least two measurement sessions, each with at least one selected wavelength of incident light and at least two different polarization states of the detected light. The detection of light beams with different polarization states within each measurement session may be timely separated by utilizing a single detector unit (FIGS. 2A–2C), or may be performed simultaneously two detector units (FIGS. 2D and 2E). The control unit 30 receives the measured data from the detector(s) and analyzes the received data to determine the glucose concentration, as will be described more specifically further below.

Figure 3:
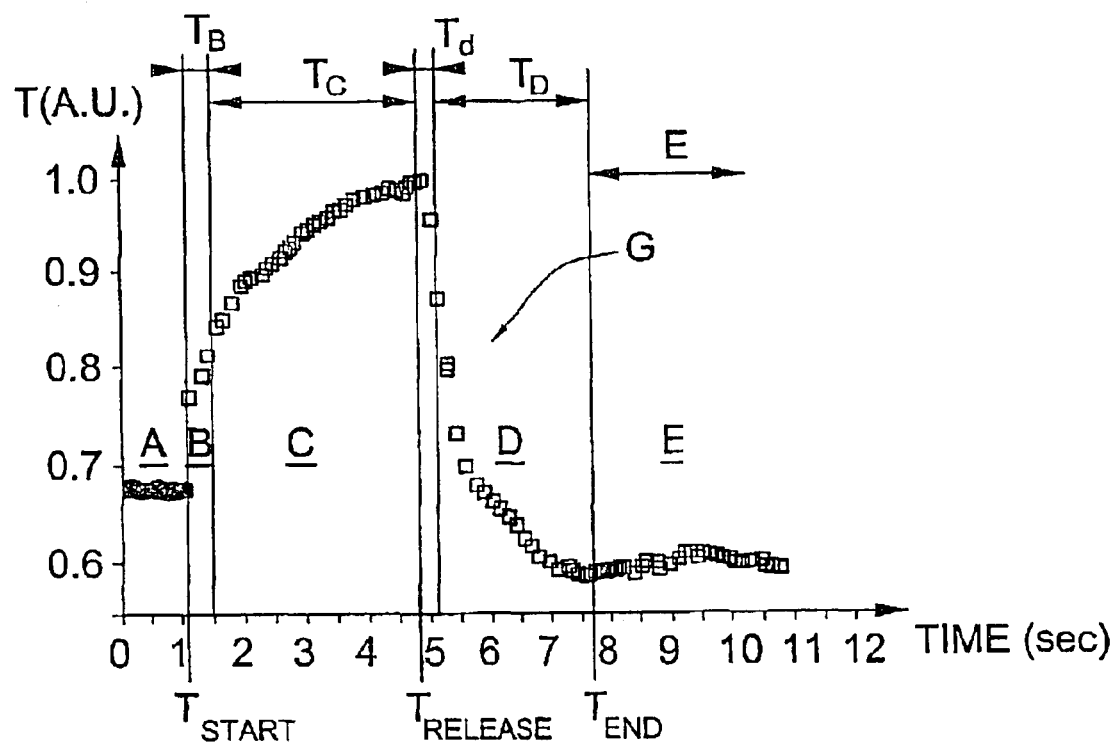
FIG. 3 illustrates a time dependence of light response of a blood containing medium, at an occlusion-release mode of operation of the measurement device according to the invention.

Reference is now made to FIG. 3, illustrating the principles of the occlusion-release operational mode. A graph G presets experimental results obtained by applying the occlusion-release technique to the patient's blood perfused fleshy medium, showing how the light-admitting characteristic of blood changes under the application of the over-systolic pressure. The transmitting characteristic are shown here as the so-called "Relative Transmission", i.e., in Transmission Arbitrary Units or T(A.U.).

The application of the over-systolic pressure sts at a moment $T_{start}$, and is maintained for a period of time so as not to cause irreversible changes in the fleshy medium (e.g., 4 seconds). The pressure is released at the moment $T_{release}$. Measurements of the Relative Transmission are performed continuously, starting prior to the application of the over-systolic pressure. Different states of the blood flow, designated A, B C, D and E, are observed State A is a state of normal blood flow before the over-systolic pressure is applied. As shown, this state is characterized by a standard fluctuating value of the relative light transmission of blood State B stars at the moment $T_{start}$(when the pressure is initially applied) and exists during a short period of time $T_B$ (about 0.5 sec) within which the over-systolic pressure is actually applied. Measurements taken during this time period should be disregarded, due to the unavoidable influence of motional and/or other artifacts causing non-monotonic fluctuations of the light transmission.

State C is a state of the temporary cessation of blood flow which lasts within a time period $T_C$ between a moment determined as ($T_{start}+T_B$) and the moment $T_{release}$. During this period of time, $T_C$, the ascending curve (or descending curve depending on the incident wavelength) of relative light transmission of blood is observed. It reaches its maximum, and may last for about 2–5.5 sec (generally, from one second to several minutes).

It is appreciated that when over-systolic pressure is applied to any proximal part of the body, there is still sufficient space for the redistribution of blood between the exact area of the measurement (ie., the measurement location, where the detector is located) and the adjacent areas in close proximity to the detector. For example, if the detector is located on a fingertip and over-systolic pressure is applied on the palm, there is enough space between the fingertip and the margin of the applied pressure to "squeeze" the blood flow from one location to another.

State D is a transitional state of blood flow which takes place after releasing the over-systolic pressure. This state starts with a slight delay $T_d$ (approximately 0.5 sec), i.e. at the moment determined as ($T_{release}+T_d$). During the time period $T_D$ of the duration of state D, the relative transmission of blood monotonously descends until it reaches values character of the normal blood flow. Such a moment is masked as $T_{end}$ in the drawing. The end of state D, and the beginning of state E, is detected when the changes of the light transmission become periodic and minimal (about 2%). State E is a state of normal blood flow, which is similar to state A.

According to the invented method of optical measurements, measured data is obtained in the form of at least two time variations (evolutions) of light response of the medium corresponding to different polarization states of the detected light, respectively. The operating wavelength for the determination of glucose concentration is selected in the visual or near infrared spectra, e.g., 660 nm. It should be noted that by appropriately selecting the wavelength of incident light, the concentration of a specific substance of interest could be determined, e.g., 1,5–2 μm for the determination of cholesterol.

It should also be noted that to obtain the time variation of the light response, either two or more timely-separated measurement sessions are taken, or one long measurement session is performed, such that at least one measurement point (moment of time) corresponds to either the state C of temporary cessation of the blood flow, or the state D of transitional blood flow, i.e., within a time period including these two states ($T_C+T_D$).

Figure 4:
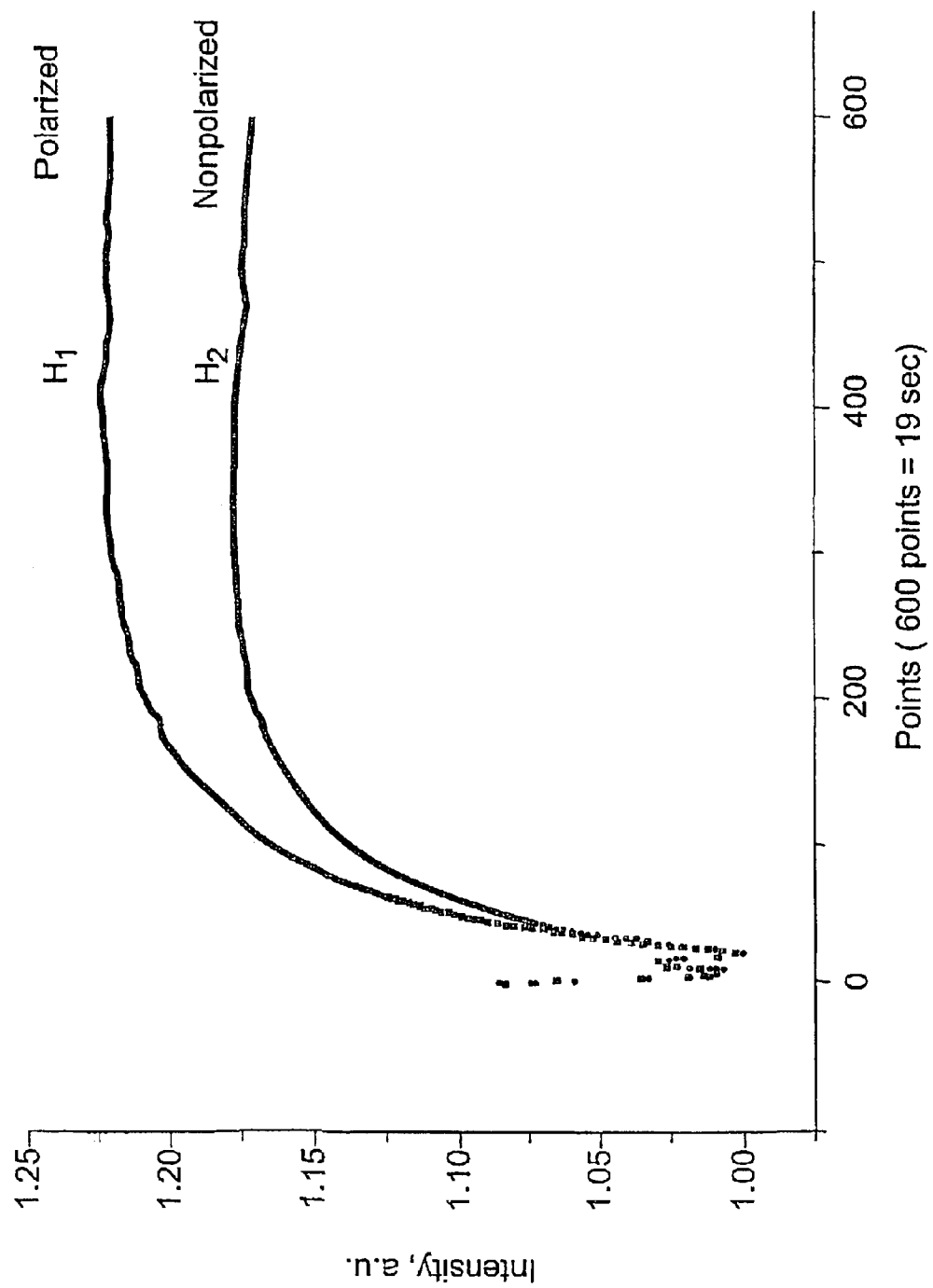
FIG. 4 graphically illustrates the experimental results of the operation of the device of FIG. 1A (in vivo), in the form of two time variations of the light responses of the medium corresponding to two different polarization states of detected light; respectively.

Turning now to FIG. 4, there are illustrated experimental results of the operation of the measurement system 1 (in vivo) designed so as to provide linear polarized and unpolarized detected light. Two graphs $G_1$ and $G_2$ are presented, each showing the time variation of the light response of the medium under measurements, namely, $T_1(t)$ and $T_2(t)$. Graph $G_1$ is obtained with the polarized incident light (beam $B_1'$ in FIG. 2A), and graph $G_2$ is obtained with the unpolarized incident light (beam $B_1$), the two graphs corresponding to different polarization states of the detected light responses, respectively.

As shown, the light responses corresponding to different polarization states of the detected light differently vary with time, depending on the polarization state of the incident light. This is due to the fact that glucose is a scattering affecting and optically active substance in blood. It affects the orientation of the vector of polarization of the polarized incident light thereby affecting the amount of light reaching the detector (passing through the analyzer).

Figure 5A:
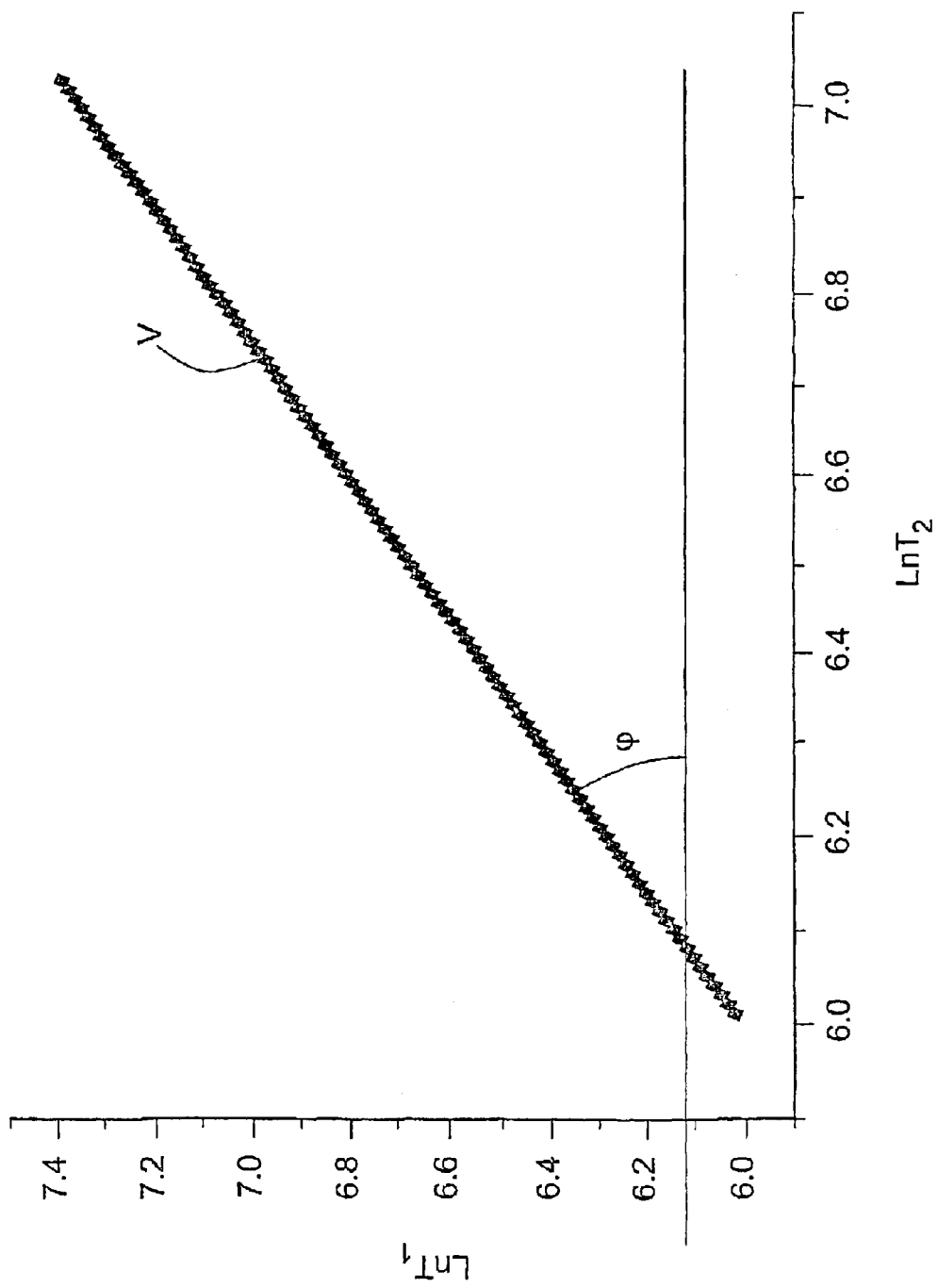
FIG. 5A graphically illustrates the relation between the two curves in FIG. 4 in logarithmic coordinates for the same value of actual glucose concentration, used for the determination of a parametric slope.

To plot a curve indicative of the relation between the different light responses (i.e., with different polarization states) affected by the same concentration of glucose $C_{gl}$, a relation between the above two time variations is determined. FIG. 5A illustrates such a curve V (shown in logarithmic coordinates) obtained from the graphs $G_1$ and $G_2$ of FIG. 4. The graph CV is a substantially straight line, the tangent of the angle of inclination φ of this line with respect to the abscissa axis presents a parametric slope, constituting a measurable parameter R.

Figure 5B:
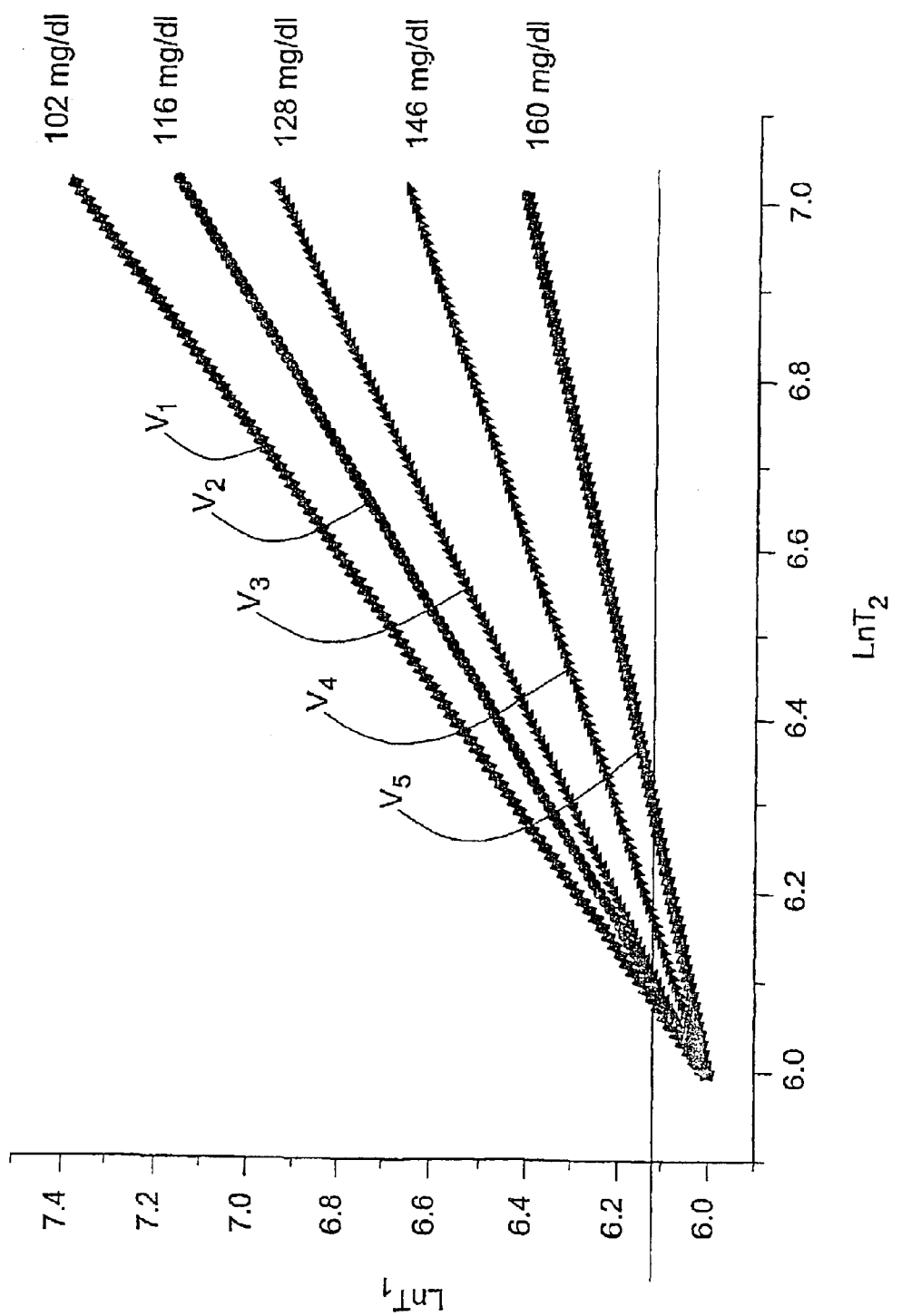
FIG. 5B illustrates different graphs with different parametric slopes corresponding to different values of the concentrations of glucose, respectively.

FIG. 5B shows a set of curves—five curves $V_1$–$V_5$ in the present example, presenting the experimental results of applying the technique of the present invention to blood samples with different known values of the concentration of glucose, i.e., 102 mg/dl; 116 mg/dl; 128 mg/dl; 146 ng/dl and 160 mg/dl. It is evident that each of these curves is characterized by a different value of the parametric slope R, as compared to the others.

Figure 6:
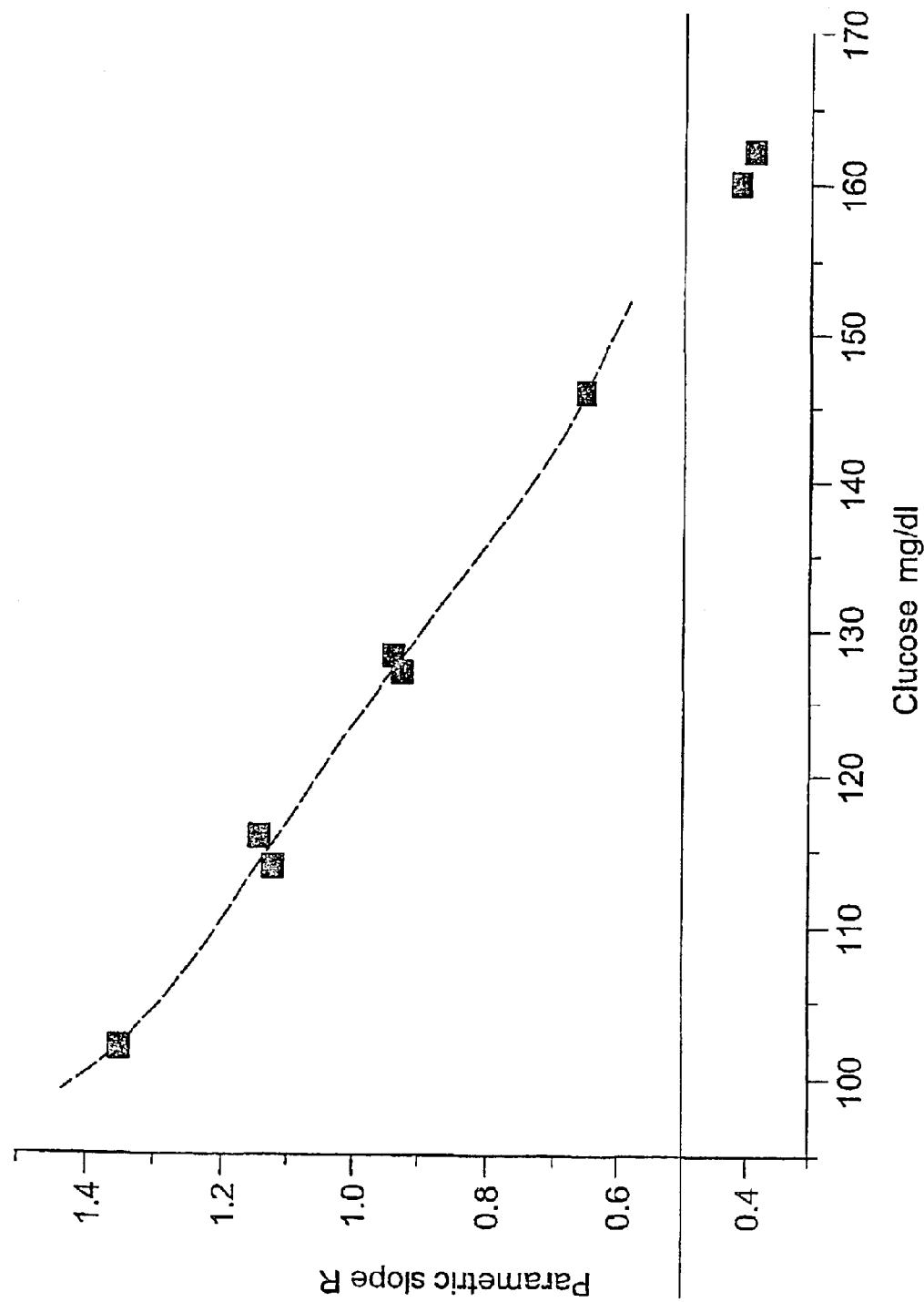
FIG. 6 illustrates a calibration curve obtained from the graphs of FIG. 5B, and used for determining the level of glucose in the patient's blood.

The graphs $V_1$–$V_5$ are used for preparing reference data in the form of a calibration curve $C_{cal}$ shown ill FIG. 6. The calibration curve is initially prepared either with respect to each specific patient at different conditions of the concentration of glucose, or with respect to various patients with different glucose concentrations in blood.

Utilizing the mewed data illustrated in FIG. 5A ($T_1(t)$ and $T_2(t)$) obtained by applying the measurements of the present invention to the specific patient, and the calibration curve $C_{cal}$ of FIG. 6, the glucose concentration $C_{gl}$ in the patient's blood can be determined. In his specific example, the parametric slope R is equal to 1.27, and, consequently, for the glucose concentration, we have: $C_{gl}$=102 mg/dl.

Figure 7:
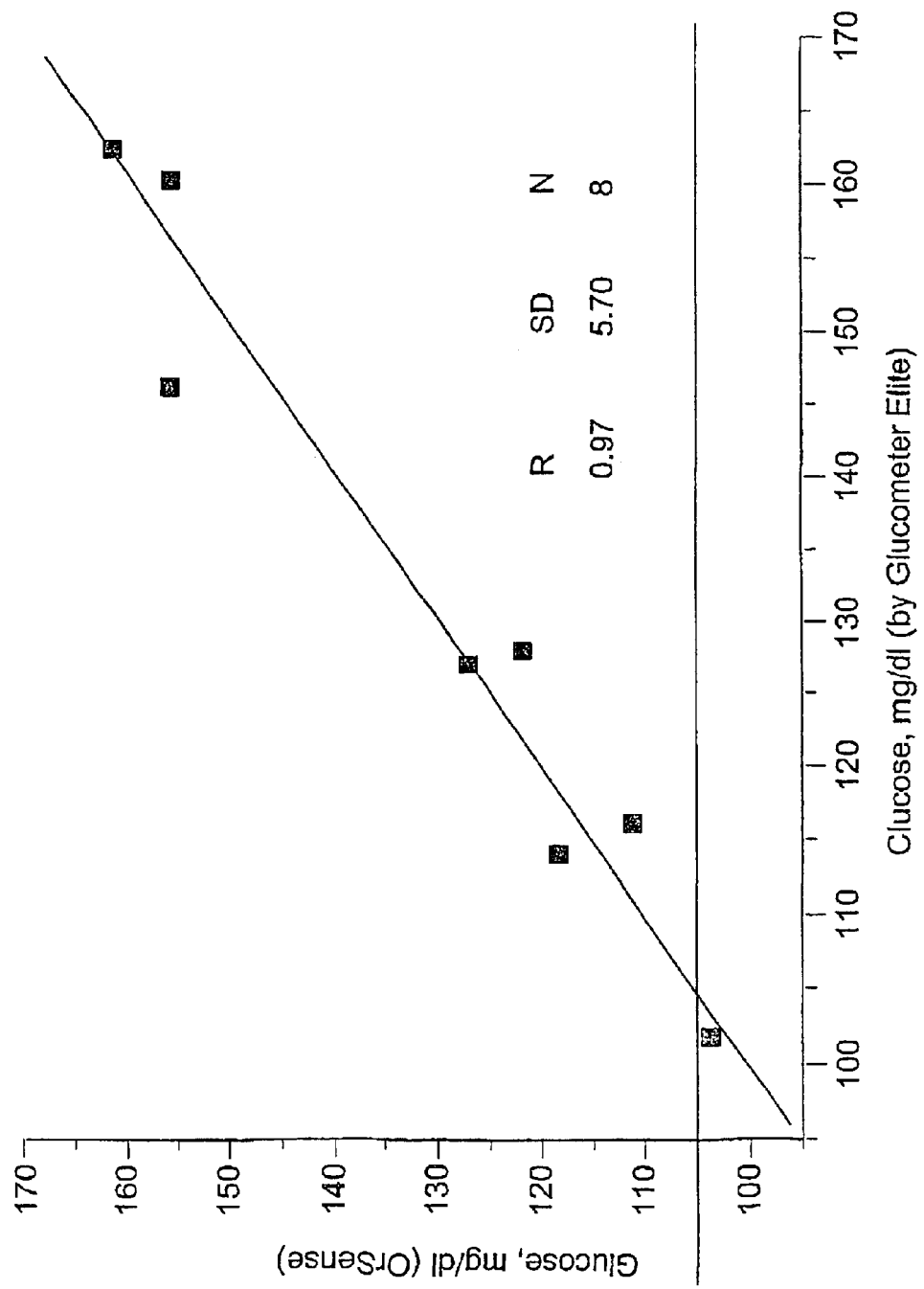
FIG. 7 illusions the correlation between the measurements of glucose concentration obtained by the measurement device according to the invention and by the standard glucometer "Elite".

FIG. 7 illustrates the correlation between the measurements of glucose concentration obtained by the measurement device according to the invention and those obtained by the standard glucometer "Elite".

As indicated above, the measurable parameter R enabling the determination of the concentration of substance in blood by using a calibration curve may be the degree of depolarization in the detected light i.e., $(T_1-T_2)/(T_1+T_2)$, which is the function of time, and varies from wavelength to wavelength. It should be understood, although not specifically shown, that a corresponding calibration curve will be in the form of the degree of depolarization as the function of glucose concentration.

It should also be noted, although not specifically shown, that to increase the accuracy of measurements, each measurement session may include the illumination of the measurement location with more than one wavelength of incident radiation (either sequentially or simultaneously, depending on the design of the measurement unit), provided that for each wavelength, two different polarization states of the detected light are obtained. Additionally, the occluder can be operated so as to provide the so-called multiple occlusion-release sessions, and measurements are taken during each of the occlusion-release cycles for one or more wavelengths of incident light.

Those skilled in the art will readily appreciate that various modifications and changes can be applied to the embodiments of the invention as hereinbefore exemplified without departing from its scope defined in and by the appended claims.

What is claimed is:

1. A method of optical measurements for use in determining the concentration of a substance in a patient's blood, the method comprising creating a state of blood flow cessation at the measurement location by applying pressure to a location on the blood containing medium upstream of said measurement location with respect to the blood flow direction, and maintaining said state for a certain cessation time, during a certain time period including said certain cessation time, performing optical measurement sessions on the measurement location by illuminating the measurement location with incident light of at least one selected wavelength, detecting, at each measurement session, at least two light responses of the medium characterized by at least two different polarization states of detected light, respectively, and generating data representative thereof; and obtaining measured data in the form of at least two time variations of the light responses of the medium, a relation between the time variations of the light responses being indicative of the concentration of the substance in blood.

2. A method of non-invasive optical measurements for use in determining the concentration of a substance in a patient's blood, the method comprising: creating a state of blood flow cessation at a measurement location in the patient's blood perfused fleshy medium by applying over-systolic pressure to the medium at a location upstream of said measurement location with respect to the blood flow direction, and maintaining said state for a certain cessation time being insufficient for irreversible changes in the fleshy medium; during a certain time period including said certain cessation time, performing optical measurement sessions at the measurement location by illuminating the measurement location with incident light of at least one selected wavelength, detecting, at each measurement session, at least two light responses of the medium characterized by at least two different polarization states of detected light, respectively, and generating data representative thereof; and obtaining measured data in the form of at least two time variations of the light responses of the medium, a relation between the time variations being indicative of the concentration of the substance in blood.

3. The method according to claim 1, wherein said substance is optically active or scattering affecting substance.

4. A method of optical measurements for determining the concentration of a substance in a patient's blood, the method comprising the steps of:
creating a state of blood flow cessation within a measurement location in a blood flow containing medium, and maintaining said state during a certain cessation time;
performing optical measurement sessions within a time period including said certain cessation time, the optical measurements including illumination of the measurement location with incident light of at least one selected wavelength, detection, at each measurement session, of at least two light responses of the medium characterized by at least two different polarization states of detected light, respectively, and generation of data representative thereof;
obtaining measured data in the form of at least two time variations of the light responses of the medium, a relation between the time variations being indicative of the concentration of the substance in blood.

5. The method according to claim 4, wherein said substance is optically active or scattering affecting substance.

6. The method according to claim 5, wherein said substance is glucose.

7. The method according to claim 5, wherein said at least one selected wavelength is in the range of visual or near infrared spectra.

8. The method according to claim 4, wherein the measurements are performed in vitro.

9. The method according to claim 4, wherein the measurements are performed in vivo.

10. The method according to claim 4, wherein said relation between the time variations is a parametric slope of a curve, which is in the form of one light response as the function of the other.

11. The method according to claim 4, wherein said relation between the time variations is degree of depolarization calculated as a ratio between the difference of light responses' intensities and their sum.

12. The method according to claim 4, wherein the optical measurements during each of the measurement sessions comprises:
illuminating the medium with at least two incident beams having different polarization states, such as to produce at least two output light beams coming from the illuminated medium; and
directing the output light beams towards a detector unit through an analyzer whose plane of preferred polarization is specifically oriented with respect to that of the incident beams.

13. The method according to claim 4, wherein the optical measurements during each of the measurement sessions comprises:
illuminating the medium with a beam of incident light having a certain state of polarization, such as to produce an output light beam coming from the illuminated medium; and
directing the output light beam towards two detector units, such that only one light component of the output light beam is directed towards a corresponding one of the detector units through an analyzer whose plane of preferred polarization is specifically oriented with respect to that of the incident beam, while the other light component of the output light beam is directly detected by the other detector unit.

14. The method according to claim 4, wherein the optical measurements during each of the measurement sessions comprises:
illuminating the medium with a beam of incident light having a certain state of polarization, so as to produce an output light beam coming from the illuminated medium;
directing the output light beam towards two detector units through two analyzer units, respectively, the analyzer units having planes of preferred polarization oriented differently to each other and to that of the incident beam.

15. A method of optical measurements for non-invasively determining the concentration of a substance in a patient's blood, the method comprising the steps of:
applying over-systolic pressure to a location on the patient's blood perfused fleshy medium, thereby creating a state of blood flow cessation within a measurement location downstream of the location of application of pressure, and maintaining said state during a certain cessation time;
performing optical measurement sessions within a time period including said certain cessation time, the optical measurements including illumination of the measurement location with incident light of at least one selected wavelength, detection, at each measurement session, of at least two light responses of the medium characterized by at least two different polarization states of detected light, respectively, and generation of data representative thereof;
obtaining measured data in the form of at least two time variations of the light responses of the medium, a relation between the time variations being indicative of the concentration of the substance in blood.

16. A method for determining the concentration of a scattering affecting or optically active substance in a patient's blood, the method comprising the steps of:
(i) providing reference data indicative of a preset measurable parameter as a function of values of said concentration;
(ii) creating a state of blood flow cessation within a measurement location in a blood flow containing medium, and maintaining said state during a certain cessation time;
(iii) performing optical measurement sessions within a time period including said certain cessation time, the optical measurements including illumination the measurement location with incident light of at least one selected wavelength, detection, at each measurement session, of at least two light responses of the medium characterized by at least two different polarization states of detected light, respectively, and generation of measured data representative thereof;
(iv) utilizing the measured data for obtaining measurement results in the form of at least two kinetic curves of the light responses of the medium as functions of time corresponding to the different polarization states of the detected light;

(v) analyzing said at least two kinetic curves for calculating said certain measurable parameter indicative of relation between them; and (vi) utilizing the calculated value and said reference data for determining the concentration of the substance in the patient's blood.

17. The method according to claim 16, wherein said substance is glucose.

18. The method according to claim 16, wherein said at least one selected wavelength is in the range of visual or near infrared spectra.

19. The method according to claim 16, wherein said reference data comprises a calibration curve obtained by applying steps (b) to (e) to blood containing media with different known values of the concentration of said substance.

20. The method according to claim 16, wherein the measurements are performed in vitro.

21. The method according to claim 16, wherein the measurements are performed in vivo.

22. The method according to claim 21, wherein said measurement location is located at the patient's finger.

23. The method according to claim 16, wherein said certain measurable parameter is a parametric slope of a curve, which is in the form of one light response as the function of the other.

24. The method according to claim 16, wherein said certain measurable parameter is degree of depolarization calculated as a ratio between the difference of the light responses' intensities, and their sum.

25. The method according to claim 16, wherein, in step (c), the optical measurements during each of the measurement sessions comprises:

illuminating the medium with at least two incident beams having different polarization states, such as to produce at least two output light beams coming from the illuminated medium;

directing the output light beams towards a detector unit through an analyzer whose plane of preferred polarization is specifically oriented with respect to that of the incident beams.

26. The method according to claim 16, wherein, step (c), the optical measurements during each of the measurement sessions comprises:

illuminating the medium with a beam of incident light having a certain state of polarization, such as to produce an output light beam coming from the illuminated medium;

directing the output light beam towards two detector units, such that only one light component of the output light beam is directed towards a corresponding one of the detector units through an analyzer whose plane of preferred polarization is specifically oriented with respect to that of the incident beam, while the other light component of the output light beam is directly detected by the other detector unit.

27. The method according to claim 16, wherein, in step (c), the optical measurements during each of the measurement sessions comprises:

illuminating the medium with a beam of incident light having a certain state of polarization, so as to produce an output light beam coming from the illuminated medium;

directing the output light beam towards two detector units through two analyzer units, respectively, the analyzer units having planes of preferred polarization oriented differently to each other and to that of the incident beam.

28. A method for non-invasively determining the concentration of a substance in a patient's blood, the method comprising the steps of:

providing reference data indicative of a preset measurable parameter as a function of values of said concentration;

applying over-systolic pressure to a location of the patient's blood perfused fleshy medium, thereby creating a state of blood flow cessation within a measurement location downstream of the location of application of pressure with respect to the blood flow direction, and maintaining said state of the blood flow cessation during a certain cessation time being insufficient for irreversible changes in the fleshy medium;

performing optical measurement sessions within a time period including said certain cessation time, the optical measurements including illumination of the measurement location with incident light of at least one selected wavelength, detection, at each measurement session, of at least two light responses of the medium characterized by at least two different polarization states of detected light, respectively, and generation of data representative thereof;

utilizing the measured data for obtaining measurement results in the form of at least two kinetic curves of the light responses of the medium as functions of time corresponding to the different polarization states of the detected light;

analyzing said at least two kinetic curves for calculating said certain parameter indicative of relation between them, and utilizing the calculated value and said reference data for determining the concentration of the substance in the patient's blood.

29. An optical measurement system for obtaining data indicative of the concentration of a scattering affecting or optically active substance in patient's blood, the system comprising:

(a) a measurement device comprising a pressurizing assembly and a measuring unit, wherein the pressurizing assembly has a pressing member for wrapping a region on a blood flow containing medium that is operable for applying over-systolic pressure to said region so as to create a state of blood flow cessation at a measurement location in the medium, and the measuring unit is operable for performing optical measurement sessions at said measurement location, and comprises an illumination system for illuminating the measurement location with specifically polarized light of at least one selected wavelength during at least two measurement sessions, and a light collection/detection system for applying polarization filtering to light propagating from the measurement location, thereby enabling detecting, at each measurement session, at least two light responses of the medium characterized by the same wavelength and at least two different polarization states, respectively, and generating measured data representative thereof; and (b) a control unit connectable to the measurement device for selectively operating said measuring unit and said pressurizing assembly, such that the state of blood flow cessation is maintained during a certain cessation time and the optical measurement sessions are performed during a time period within said certain cessation time, the control unit being responsive to said measured data to determine time variations of the light responses of the medium corresponding to said at least two different polarization states of the detected light, analyze the time variations for determining a preset parameter measured as a relation between the time variations, and being indicative of the time variation of depolarization of light caused by the scattering affecting or optically active substance in the medium.

30. The system according to claim 29, wherein
the illumination system comprises an illuminator operable for generating at least one beam of incident light of the selected wavelength, and a polarizer unit,
the light collection/detection system comprises at least one detector unit and at least one analyzer, a plane of preferred polarization of said at least one analyzer being specifically oriented with respect to that of the polarizer unit, said at least one detector unit detecting the light responses of the medium and generating the measured data indicative thereof.

31. The system according to claim 29, wherein said substance is glucose.

32. The system according to claim 29, wherein the measurement location is located at the patient's finger.

33. The system according to claim 29, wherein the measurement location is located inside a flow cuvette through which the flow of patient's blood sample is drawn.

34. The system according to claim 32, wherein said pressing member of the pressurizing assembly is a cuff for wrapping the patient's finger, squeezing of the cuff being operated by a drive coupled to the control unit.

35. The system according to claim 29, wherein the pressurizing assembly comprises a peristaltic pump operated by a drive coupled to the control unit.

36. The system according to claim 30, wherein
said illuminator is operable to produce two beams of light, and said polarizer unit comprises at least one polarizer accommodated in optical path of one of said two beams, thereby producing two incident beams of different polarization state, respectively, and producing two output beams coming from the illuminated medium;
the collection/detection system comprises the single analyzer accommodated in optical path of the output light propagating towards the single detector unit.

37. The system according to claim 30, wherein
said illuminator is operable to produce two beams of light, and said polarizer unit comprises a polarizer accommodated in the optical path of each of said two beams, and a retarder accommodated in the optical path of each of said two beams and operable with different operational modes with respect to said two beams, the illuminator thereby producing two incident beams of different polarization states, respectively;
the collection/detection system comprises the single analyzer accommodated in optical path of the output light propagating towards the single detector unit.

38. The system according to claim 30, wherein
said illuminator is operable to generate a beams of light, and said polarizer unit comprises a polarizer accommodated in optical path of the generated beam propagating towards the medium, thereby producing output light coming from the illuminated medium;
the collection/detection system comprises two detector units for detecting two spatially separated light components of the output light, two analyzers being accommodated in optical path of said two light components, respectively, propagating towards the detection units, the analyzers having different orientation of planes of preferred polarization.

39. The system according to claim 29, wherein said preset measurable parameter is a parametric slope of a curve, which is in the form of one light response as the function of the other.

40. The system according to claim 29, wherein said preset measurable parameter is degree of depolarization calculated as a ratio between the difference of the light responses' intensities, and their sum.

41. The system according to claim 29, wherein
the control unit operates said pressurizing assembly, such that said cessation time during which the over-systolic pressure is applied is insufficient for irreversible changes in the fleshy medium.

42. The device according to claim 29, wherein said at least one selected wavelength is in the range of visual or near infrared spectra.

43. A measurement system for non-invasively determining the concentration of a substance in a patient's blood, the system comprising:
a measurement device that comprises a pressurizing assembly operable to apply over-systolic pressure to a location on the patient's blood perfused fleshy medium, so as to create a state of blood flow cessation at a measurement location in the medium located downstream of the location of application of pressure; and comprises a measuring unit operable to perform optical measurement sessions to said measurement location, the measuring unit comprising an illumination system and a light collection/detection system which are operable so as to detect at least two light responses of the medium characterized by at least two different polarization states of detected light, respectively, and generate measured data representative thereof; and
a control unit connectable to the measurement device for selectively operating said measuring unit and said pressurizing assembly, such that the state of blood flow cessation is maintained during a certain cessation time being insufficient for irreversible changes in the fleshy medium, and the optical measurement sessions are performed within a time period including said cessation time, the control unit being responsive to said measured data to determine time variations of said at least two light responses of the medium corresponding to at least two different polarization states of the detected light, analyze the time variations for determining a preset parameter measured as a relation between the time variations, and determining the concentration of said substance using reference data indicative of the preset measurable parameter as a function of values of the substance concentration.

44. A measurement device for performing non-invasive optical measurements for determining the concentration of a substance in patient's blood, the device comprising:
a pressurizing assembly operable to apply over-systolic pressure to a location on the patient's blood perfused fleshy medium, so as to create a state of blood flow cessation at a measurement location in the medium located downstream of the location of application of pressure, and to maintain said state during a certain cessation time being insufficient for irreversible changes in the fleshy medium; and
a measuring unit operable to perform optical measurement sessions at said measurement location within a time period including said cessation time, the measuring unit comprising an illumination system and a light collection/detection system which are operable to detect, at each measurement session, at least two light responses of the medium characterized by at least two different polarization states of detected light, respectively, and generate measured data representative thereof, the measured data being indicative of time variations of said at least two light responses of the medium corresponding to at least two different polarization states of the detected light, a relation between said time variations being indicative of the concentration of said substance.

45. The device according to claim 44, wherein said substance is optically active or scattering affecting substance.

46. The device according to claim 45, wherein said substance is glucose.

47. The device according to claim 44, wherein said at least one selected wavelength is in the range of visual or near infrared spectra.

48. The device according to claim 44, wherein the pressurizing assembly comprises a cuff for wrapping a patient's finger, and is operable for squeezing the cuff.

49. The device according to claim 44, wherein said illumination system comprises an illuminator operable to produce two beams of light, and a polarizer unit that comprises at least one polarizer accommodated in optical path of one of said two beams, thereby producing two incident beams of different polarization state, respectively, and producing two output beams coming from the illuminated medium;

the light collection/detection system comprises a single analyzer accommodated in optical path of the output light propagating towards a single detector unit.

50. The device according to claim 44, wherein said illumination system comprises an illuminator operable to produce two beams of light, and a polarizer unit that comprises a polarizer accommodated, in the optical path of each of said two beams, and a retarder accommodated in the optical path of each of said two beams and operable with different operational modes with respect to said two beams, the illuminator thereby producing two incident beams of different polarization states, respectively;

the light collection/detection system comprises a single analyzer accommodated in optical path of the output light propagating towards a single detector unit.

51. The device according to claim 44, wherein said illumination system comprises an illuminator operable to generate a beams of light, and a polarizer unit that comprises a polarizer accommodated in optical path of the generated beam propagating towards the medium, thereby producing output light coming from the illuminated medium;

the light collection/detection system comprises two detector units for detecting two spatially separated light components of the output light, two analyzers being accommodated in optical path of said two light components, respectively, propagating towards the detection units, the analyzers having different orientations of planes of preferred polarization.

52. The device according to claim 44, wherein said relation between the time variations is a parametric slope of a curve, which is in the form of one light response as the function of the other.

53. The device according to claim 44, wherein said relation between the time variations is degree of depolarization calculated as a ratio between the difference of light responses' intensities and their sum.

* * * * *